United States Patent
Bharat et al.

(10) Patent No.: US 11,457,897 B2
(45) Date of Patent: Oct. 4, 2022

(54) ULTRASOUND TRANSDUCER TILE REGISTRATION

(71) Applicant: KONINKLIJKE PHILIPS N.V., Eindhoven (NL)

(72) Inventors: Shyam Bharat, Arlington, MA (US); Ramon Quido Erkamp, Swampscott, MA (US); Man Nguyen, Melrose, MA (US); Jun Seob Shin, Medford, MA (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 427 days.

(21) Appl. No.: 16/334,869

(22) PCT Filed: Sep. 20, 2017

(86) PCT No.: PCT/EP2017/073766
§ 371 (c)(1),
(2) Date: Mar. 20, 2019

(87) PCT Pub. No.: WO2018/054969
PCT Pub. Date: Mar. 29, 2018

(65) Prior Publication Data
US 2020/0022680 A1     Jan. 23, 2020

Related U.S. Application Data

(60) Provisional application No. 62/396,852, filed on Sep. 20, 2016.

(30) Foreign Application Priority Data

Oct. 19, 2016    (EP) ..................................... 16194511

(51) Int. Cl.
*A61B 8/08*        (2006.01)
*G06T 7/33*        (2017.01)
(Continued)

(52) U.S. Cl.
CPC .......... *A61B 8/5253* (2013.01); *A61B 8/0841* (2013.01); *A61B 8/4272* (2013.01);
(Continued)

(58) Field of Classification Search
None
See application file for complete search history.

(56) References Cited

U.S. PATENT DOCUMENTS 4,870,867 A * 10/1989 Shaulov ................ B06B 1/0629
                                                                     73/625
2007/0078345 A1    4/2007   Mo et al.
(Continued)

FOREIGN PATENT DOCUMENTS

| CN | 102869308 A | 1/2013 |
| WO | 0200093 A2 | 1/2002 |
| WO | 2004019799 A2 | 3/2004 |

OTHER PUBLICATIONS

Hughes et al., "Parallel and Distributed Programming Using C++", published Aug. 25, 2003 by Addison-Wesley Professional, chapter 1, section 1.2 (Year: 2003).*
(Continued)

*Primary Examiner* — Colin T. Sakamoto

(57) ABSTRACT

An ultrasound imaging system (1) comprises an ultrasound transducer array (100) comprising a plurality of ultrasound transducer tiles (101*a-d*), each of said tiles having an independently adjustable orientation such as to conform an ultrasound transmitting surface to a region of a body (50) including a foreign object such as a pacemaker, a stent, or an interventional tool (200). Using a known spatial arrange-
(Continued)

ment of a plurality of features (201-204) of the foreign object (200), the respective ultrasound images generated by the ultrasound transducer tiles are registered in order to generate a composite image, in which the position and orientation of the foreign object in the individual images is superimposed. The position and orientation of an interventional tool may be determined for each image using object recognition algorithms or using acoustic feedback information provided by at least three ultrasound sensors (201-204) arranged in a known spatial arrangement on the interventional tool.

12 Claims, 10 Drawing Sheets

(51) Int. Cl.
  *G01S 15/89* (2006.01)
  *A61B 8/00* (2006.01)
  *A61B 17/34* (2006.01)

(52) U.S. Cl.
  CPC ........ *A61B 8/4494* (2013.01); *G01S 15/8925* (2013.01); *G01S 15/8934* (2013.01); *G06T 7/33* (2017.01); *A61B 2017/3413* (2013.01); *G01S 15/8995* (2013.01)

(56) References Cited

U.S. PATENT DOCUMENTS

| | | | |
|---|---|---|---|
| 2007/0255137 A1* | 11/2007 | Sui ...................... | G01S 15/8993 600/443 |
| 2008/0249419 A1 | 10/2008 | Sekins et al. | |
| 2009/0003675 A1 | 1/2009 | Moreau-Gobard | |
| 2009/0024034 A1 | 1/2009 | Moreau-Gobard et al. | |
| 2011/0201931 A1 | 8/2011 | Palmeri et al. | |
| 2015/0269728 A1 | 9/2015 | Parthasarathy et al. | |
| 2015/0359512 A1* | 12/2015 | Boctor ................... | A61B 8/469 600/444 |
| 2015/0374335 A1* | 12/2015 | Brown ................ | G01S 15/8993 600/447 |
| 2016/0045184 A1* | 2/2016 | Courtney ............... | A61B 8/483 600/424 |
| 2016/0324501 A1* | 11/2016 | Vignon .................. | A61B 8/461 |

OTHER PUBLICATIONS

Singh, et al., "Development of an ultrasound imaging system for needle guidance", 2009 IEEE International Ultrasonics Symposium Proceedings, pp. 1852-1855.

Daft, C., "Comfortable transducers for large-volume operator-independent imaging", 2010 IEEE International Ultrasonics Symposium Proceedings, pp. 798-808.

International Search Report and Written Opinion for International Application No. PCT/EP2017/073766, dated Oct. 27, 2017, 14 pages.

* cited by examiner

ULTRASOUND TRANSDUCER TILE REGISTRATION

This application is the U.S. National Phase application under 35 U.S.C. § 371 of International Application No. PCT/EP2017/073766, filed on Sep. 20, 2017, which claims the benefit of both Provisional Application Serial No. 62,396,852, filed Sep. 20, 2016, and European Application Serial No. 16194511.8, filed Oct. 19, 2016. These applications are hereby incorporated by reference herein.

FIELD OF THE INVENTION

The present invention relates to an ultrasound imaging system comprising an ultrasound transducer array comprising a plurality of ultrasound transducer tiles, each of said tiles having an independently adjustable orientation such as to conform an ultrasound transmitting surface of the tile to a region of a body; and a user interface including a processing arrangement coupled to the ultrasound transducer array and configured to register the ultrasound transducer tiles.

The present invention further relates to a method of registering the ultrasound transducer tiles of such an ultrasound imaging system.

BACKGROUND OF THE INVENTION

Ultrasound imaging is commonly used to support interventional or investigative procedures in which a foreign object, such as an interventional tool, e.g. a catheter, biopsy needle or the like, a fixed object such as a atrial stent, cardiac pacemaker, defibrillator or the like, is imaged with the ultrasound imaging system to assist a medical professional to either perform a (minimally) invasive medical procedure or to evaluate a body portion of interest including the foreign object. In such applications, it may be necessary to accurately determine the position and orientation of the foreign object in the images produced with the ultrasound imaging system, in particular in case of interventional tools such as biopsy needles, real-time feedback about the position and orientation of the interventional tool with the ultrasound imaging system is critically important, e.g. to provide inadvertent damage to body tissue. This is for example a key concern in chorionic villus sampling, where incorrect positioning of the biopsy needle may lead to foetal damage or termination.

To this end, the ultrasound transducer of the ultrasound imaging system may assist in tracking a foreign object in a global coordinate system, for example by means of ultrasound sensors on the foreign object in a known spatial arrangement, where information pertaining to the ultrasound signals, e.g. beams, generated with the ultrasound transducer tiles may be detected with the ultrasound sensors to facilitate such spatial referencing of the ultrasound transducer. An example of such a technique is given in US 2015/0269728 A1, which discloses a method for mapping coordinates between images and tracking systems, and which includes providing a calibration tool having a fixed geometric shape. The calibration tool includes first sensors associated with an imaging mode and second sensors associated with a tracking mode. The first and second sensors are distributed and mounted at known locations on the fixed geometric shape. The first sensors are located in a field of view of an imaging system to determine a position of the calibration tool in image space. The second sensors are tracked to determine a same position of the calibration tool in tracking space. The image space and the tracking space are mapped in a common coordinate system based on artefacts of the calibration tool.

However, a drawback of conventional ultrasound transducers is their limited field of view, which may be too small to image an entire foreign object, e.g. the entire interventional tool as well as their inability to obtain high image resolution at greater depths. At least some of these problems may be addressed by the use of so-called large area ultrasound transducer arrays. Such arrays typically comprise a plurality of tiles each containing a plurality of ultrasound transducers such as piezoelectric transducer elements formed of materials such as lead zirconate titanate (PZT) or polyvinylidenefluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. Such tiles for example may be chips of a semiconductor substrate in which the ultrasound transducer elements are located, which tiles may have dimensions of several centimetres squared ($cm^2$) in some applications. This allows for the ultrasound transducer arrays to cover larger areas of the subject's body to be imaged or treated. The ultrasound transducer elements of such tiles may be grouped together and operated in unison, such that the tile behaves as a composite ultrasound transducer element comprising multiple facets, i.e. ultrasound transducer cells, combining to form the composite ultrasound transducer element, or alternatively may be operated independently.

For such ultrasound transducer arrays, and in particular for large area ultrasound transducer arrays, e.g. ultrasound transducer arrays comprising a plurality of such ultrasound transducer tiles, it is far from trivial to establish a good conformal contact between the transducer elements (tiles) of the ultrasound probe, i.e. the large-area ultrasound transducer array, and the part of the body to be imaged. For smaller ultrasound probes, this is typically achieved by using special gels that improve the contact between the ultrasound transducer array and the body part. However, a drawback of this approach is that usually large amounts of gel have to be used, which may contain air bubbles that interfere with the transmission or reception of the ultrasound signals.

Also, such gel applications may no longer be practically feasible for large area ultrasound transducer arrays to solely produce the conformal and acoustic coupling required between the array and body region on which the array is placed, as it becomes practically impossible to effectively apply the gel to the individual transducer elements, e.g. tiles, without this process becoming messy due to the use of excess gel. In some cases, it even becomes impossible to achieve the desired conformal contact between the ultrasound transducer array and the surface of the body portion to receive the array, e.g. due to the relatively large curvature of the surface.

To this end, flexible ultrasound transducer arrays have entered the market, which may exhibit improved compliance with a contoured surface, e.g. a curved portion of a patient's body. For such arrays, a reduced amount of coupling gel may be used, typically to improve acoustic coupling as the desired conformal coupling is largely achieved by the flexibility of the transducer array. However, operation of such ultrasound transducer arrays is not without challenges. In such arrays, the ultrasound transducer tiles have several degrees of freedom, e.g. translational freedom in the X, Y, Z-plane as well as tip/tilt freedom. In order to achieve coherent beamforming in such scenarios, the actual orientation (relative positions) of each ultrasound transducer tile must be known to the beamforming circuitry of an ultrasound system deploying such an ultrasound transducer array, i.e. the images generated with the respective tiles must be spatially registered. This typically requires the inclusion of expensive orientation sensors associated with individual tiles.

In "Development of an ultrasound imaging system for needle guidance" by R. S. Singh et al., 2009 IEEE International Ultrasonics Symposium Proceedings, 20 September 2009, pp. 1852-1855 (XP031654735), it is there described an ultrasound imaging system that may significantly simplify ultrasound guidance procedures while producing high quality volumetric imagery. The system features an affixable thin flexible ultrasound transducer that conforms to curved body surfaces and a backward propagation-based image reconstruction technique.

SUMMARY OF THE INVENTION

The present invention seeks to provide an ultrasound imaging system having an ultrasound transducer array comprising a plurality of ultrasound transducer tiles, each of said tiles having an independently adjustable orientation such as to conform an ultrasound transmitting surface of the tile to a region of a body, wherein the ultrasound images produced by the respective tiles may be spatially registered without such orientation sensors.

The present invention further seeks to provide a method of spatially registering the ultrasound transducer tiles of such an ultrasound imaging system.

According to an aspect, there is provided an ultrasound imaging system comprising a plurality of ultrasound transducer tiles, each of said tiles having an independently adjustable orientation such as to conform an ultrasound transmitting surface of the tile to a region of a body and a user interface including a processing arrangement coupled to the ultrasound transducer array and configured to register the ultrasound transducer tiles by receiving respective ultrasound images from at least some of the ultrasound transducer tiles when the ultrasound transducer array is positioned on said region; identifying, using a known spatial arrangement of a plurality of features of a foreign object located within the body, the position and location of said foreign object in a set of received individual ultrasound images each comprising at least some of said features; and generating a composite ultrasound image from the individual ultrasound images in said set by superimposing the identified respective positions and orientations of the foreign object in the individual ultrasound images.

The present invention is based on the insight that a foreign object in the body of the patient, e.g. an intervention tool such as a biopsy needle or the like, may be used as a reference in the multiple images generated from different viewing angles with the independently adjustable ultrasound transducer tiles, such that the different orientations of the foreign object in the respective images may be used to derive orientation information of the ultrasound transducer tiles from these images, i.e. to register these images in a common reference frame, from which a composite ultrasound image may be generated to visualize a region of interest within the body including the foreign object with high accuracy, i.e. high image quality.

In an embodiment, this may be achieved by the processing arrangement further being configured to, using the respective positions and orientations of the foreign object in the individual ultrasound images, select one of said individual ultrasound images as a reference ultrasound image; define the position and orientation of the foreign object in the reference ultrasound image as a reference; and, for each other individual ultrasound image:

generate a transformation matrix for transforming the position and orientation of the foreign object in the ultrasound image to the reference; and transform the image in accordance with its transformation matrix.

Preferably, the foreign object is an interventional tool, which may form part of the ultrasound imaging system. In an embodiment, the position and orientation information of the interventional tool in the respective ultrasound images may be extracted from these images using image processing algorithms such as object recognition algorithms, which may be used to identify the features of the interventional tool in the known spatial arrangement, e.g. shape features of the interventional tool, in these images to derive the respective local spatial orientations of the interventional tool in the respective ultrasound images and register these images based on the obtained local spatial orientations.

In the above embodiment, the foreign object, e.g. the interventional tool, is a passive object in the sense that the registration process is solely based on the ultrasound images generated with the ultrasound transducer array. However, in a particularly advantageous embodiment, the features having the known spatial arrangement of the interventional tool may comprise at least three ultrasound sensors in a defined spatial arrangement on the interventional tool that can provide acoustic feedback to the ultrasound imaging system based on which the aforementioned registration process of the respective ultrasound images may be performed. To this end, the processing arrangement may be configured to receive sensor signals from at least some of said at least three ultrasound sensors, said sensor signals corresponding to ultrasound signals generated with the ultrasound transducer array from which said ultrasound images are generated; and wherein identify the position and orientation of the interventional tool in the set of received individual ultrasound images is based at least in part on said sensor signals.

For example, the processing arrangement configured to identify the position and orientation of the interventional tool in the set of received individual ultrasound images based at least in part on said sensor signals is configured to derive at least one of time of flight information and ultrasound signal amplitude information from said sensor signals; and at least identify the position and orientation of the interventional tool in an individual ultrasound image from said set at least partially based on the time of flight information and ultrasound signal amplitude information from said sensor signals corresponding to ultrasound signals from which said individual ultrasound image is generated. This facilitates a registration process at least partially and in some embodiments solely based on the acoustic feedback provided by the ultrasound sensors on the interventional tool (or other foreign object within the body containing such ultrasound sensors in a particular spatial arrangement).

In an embodiment, the processing arrangement is further configured to register the ultrasound transducer tiles by simultaneously registering a cluster of ultrasound transducer tiles, the ultrasound images generated with the tiles in said cluster containing at least three common ultrasound sensors. This is particularly advantageous in scenarios where not all ultrasound sensors are visible to each ultrasound transducer tile, such that some ultrasound transducer tiles may not have a sufficient number of ultrasound sensors in 'line of sight' (i.e. within acoustic range) to facilitate registration of their respective ultrasound images. In this manner, only adjacent (clustered) ultrasound transducer tiles seeing a sufficient amount of the same (common) ultrasound sensors of the interventional tool may be registered in a simultaneous registration process.

In a further scenario, different clusters of ultrasound transducer tiles may have a different set of common ultrasound sensors within acoustic range. In such a scenario, it may not be practically feasible for the ultrasound imaging system to receive ultrasound signals from all ultrasound sensors at the same time, for example in case the number of channels between the interventional tool and the user interface, e.g. console, of the ultrasound imaging system is limited. In such a case, the ultrasound sensors may be coupled to the processing arrangement by a multiplexer controlled by said processing arrangement, wherein the processing arrangement is configured to enable the at least three common ultrasound sensors with the multiplexer during generation of the ultrasound images with the tiles in said cluster such that only those ultrasound sensors within acoustic range of a particular cluster of ultrasound transducer tiles may be communicatively coupled to the processing arrangement of the ultrasound imaging system through the multiplexer.

In an embodiment, the ultrasound transducer array comprises a guide channel for mounting the interventional tool in the ultrasound transducer array, such that the interventional tool may be guided into the patient's body through the ultrasound transducer array. This has the advantage of achieving an orientational coupling between the ultrasound transducer array and the interventional tool such that it becomes more straightforward to maintain the interventional tool within the field of view of the ultrasound transducer array.

The processing arrangement may be further configured to, in response to a user input received at the user interface, generate a further composite ultrasound image composed with the registered ultrasound transducer tiles in said set. By only including those ultrasound images in which the foreign object, e.g. the interventional tool, is visible, a zoomed image of this object may be produced to further assist the operator of the ultrasound transducer array and/or the operator of an interventional tool to correctly guide the interventional tool by the provision of such a high-definition zoomed image.

Each ultrasound transducer tile may comprise a plurality of ultrasound transducer elements, and wherein the processing arrangement is further configured to generate the further composite ultrasound image with a selection of the ultrasound transducer elements of at least some of the registered ultrasound transducer tiles in said set, the selected ultrasound transducer elements contributing to the imaging of the foreign body in the individual ultrasound image generated with the ultrasound transducer tile. This may further improve the definition of such a zoomed image by only including those ultrasound transducer elements that contribute to visualization of the foreign object, e.g. the interventional tool.

According to another aspect, there is provided a method of registering ultrasound transducer tiles of an ultrasound imaging system comprising a plurality of said ultrasound transducer tiles, each of said tiles having an independently adjustable orientation such as to conform an ultrasound transmitting surface of the tile to a region of a body, the method comprising receiving respective ultrasound images from at least some of the ultrasound transducer tiles when the ultrasound transducer array is positioned on said region; identifying, using a known spatial arrangement of a plurality of features of a foreign object located within the body, the position and location of said foreign object in a set of received individual ultrasound images each comprising at least some of said features; and generating a composite ultrasound image from the individual ultrasound images in said set by superimposing the identified respective positions and orientations of the foreign object in the individual ultrasound images.

Such a method facilitates registration of the ultrasound images generated with such an ultrasound transducer array without requiring positional feedback information, e.g. as provided by positional sensors associated with each ultrasound transducer tile, based on the insight that the foreign object within the body of the patient may be used as a common reference to achieve such registration of the respective images.

Such registration for example may be achieved using the respective positions and orientations of the foreign object in the individual ultrasound images by selecting one of said individual ultrasound images as a reference ultrasound image; defining the position and orientation of the foreign object in the reference ultrasound image as a reference; and, for each other individual ultrasound image: generating a transformation matrix for transforming the position and orientation of the foreign object in the ultrasound image to the reference; and transforming the image in accordance with its transformation matrix.

In a preferred embodiment, the foreign object is an interventional tool and the plurality of features comprises at least three ultrasound sensors in a known spatial arrangement on the interventional tool, the method further comprising receiving sensor signals from at least some of said at least three ultrasound sensors, said sensor signals corresponding to ultrasound signals generated with the ultrasound transducer array from which said ultrasound images are generated; and wherein identify the position and orientation of the interventional tool in the set of received individual ultrasound images is based at least in part on said sensor signals. In this embodiment, the ultrasound image registration may be achieved using acoustic feedback provided by the ultrasound sensors, which acoustic feedback in combination with the known spatial arrangement of these ultrasound sensors and optionally with information extracted from the ultrasound images, e.g. using object recognition algorithms or the like, facilitates the registration of the ultrasound images without having to determine the actual position and orientation of the respective ultrasound transducer tiles responsible for the generation of these images.

Such acoustic feedback for example may include deriving at least one of time of flight information and ultrasound signal amplitude information from said sensor signals; and identifying the position and orientation of the interventional tool in an individual ultrasound image from said set at least partially based on the time of flight information and ultrasound signal amplitude information from said sensor signals corresponding to ultrasound signals from which said individual ultrasound image is generated.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
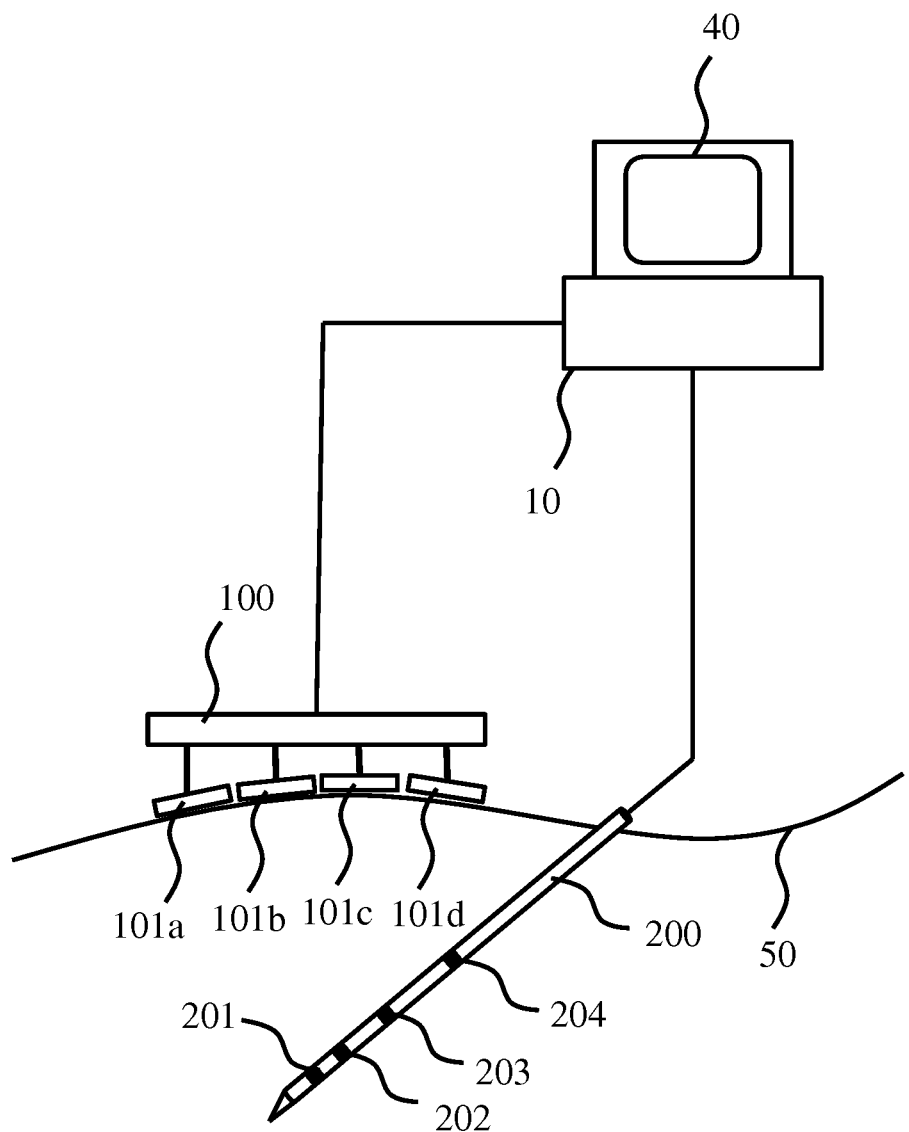
FIG. 1 schematically depicts an ultrasound imaging system according to an embodiment.

It should be understood that the Figures are merely schematic and are not drawn to scale. It should also be understood that the same reference numerals are used throughout the Figures to indicate the same or similar parts.

FIG. 1 schematically depicts an ultrasound imaging system 1 according to an embodiment of the present invention. The ultrasound imaging system 1 comprises an ultrasound transducer array 100 for positioning on a region of a body 50 of a patient for ultrasound imaging of a body portion of the patient. The ultrasound transducer array 100 comprises a plurality of ultrasound transducer tiles 101 (here schematically depicted by four individually identified ultrasound transducer tiles 101a-d by way of non-limiting example), which ultrasound transducer tiles 101 have independently adjustable orientations such as to conform an ultrasound transmitting surface of the tile to a region of a body 50, i.e. the orientation of each ultrasound transducer tile 101 is independently adjustable.

Figure 2:
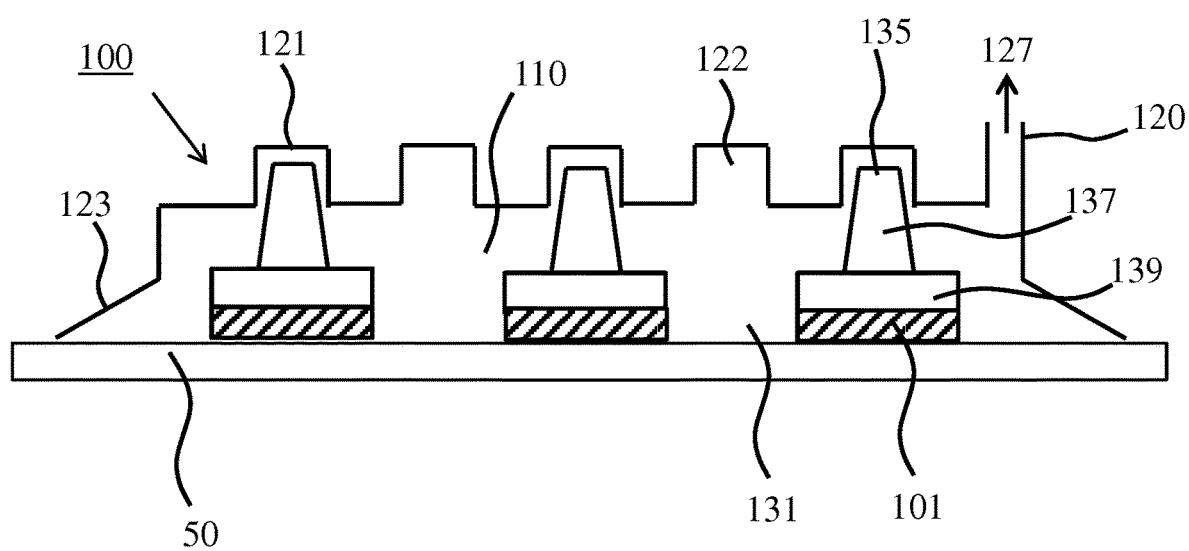
FIG. 2 schematically depicts an example embodiment of an aspect of such an ultrasound imaging system.

A non-limiting example of such an ultrasound transducer array 100 is described in more detail with the aid of FIG. 2, which schematically depicts an example embodiment of an ultrasound transducer array 100 comprising independently adjustable ultrasound transducer element tiles 101. Each tile 101 may comprise one or more ultrasound transducer elements (not shown). Each tile 101 for example may be a diced chip or the like onto which the one or more ultrasound transducer elements have been formed or mounted. In embodiments of the present invention, the ultrasound transducer elements may be implemented in any suitable manner. For example, the ultrasound transducer elements may be implemented by a piezoelectric ceramic material such as a lead zirconate titanate (PZT)-based material, a piezoelectric single crystal or composite material, a capacitive micromachined ultrasound transducer (CMUT) and so on.

The ultrasound transducer element tiles 101 may have any suitable shape, e.g. a circular shape or polygonal shape. A polygonal shape such as a rectangular, e.g. square, shape is particularly mentioned as such a shape facilitates a close packing of the ultrasound transducer element tiles 101 within the transducer array, wherein the gap 131 between adjacent ultrasound transducer element tiles 101 is minimized. The avoidance of relatively large gaps 131 between adjacent ultrasound transducer element tiles 101 ensures that a substantially continuous image may be generated with the ultrasound transducer array 100 and may at least reduce the formation of ultrasound artefacts such as grating lobes. The ultrasound transducer array 100 may have any suitable shape, e.g. may be a 1-dimensional or 2-dimensional ultrasound transducer array. The tiles 101 preferably are arranged in a 2D matrix form, such that a 3D image/volume can be formed from the ultrasound data generated and collected with the individual tiles 101. In a preferred embodiment, the ultrasound probe 100 comprises a plurality of ultrasound transducer tiles 101, each having a transducer surface area of several cm², e.g. 2-50 cm², to form a large area ultrasound transducer array 100.

Figure 3:
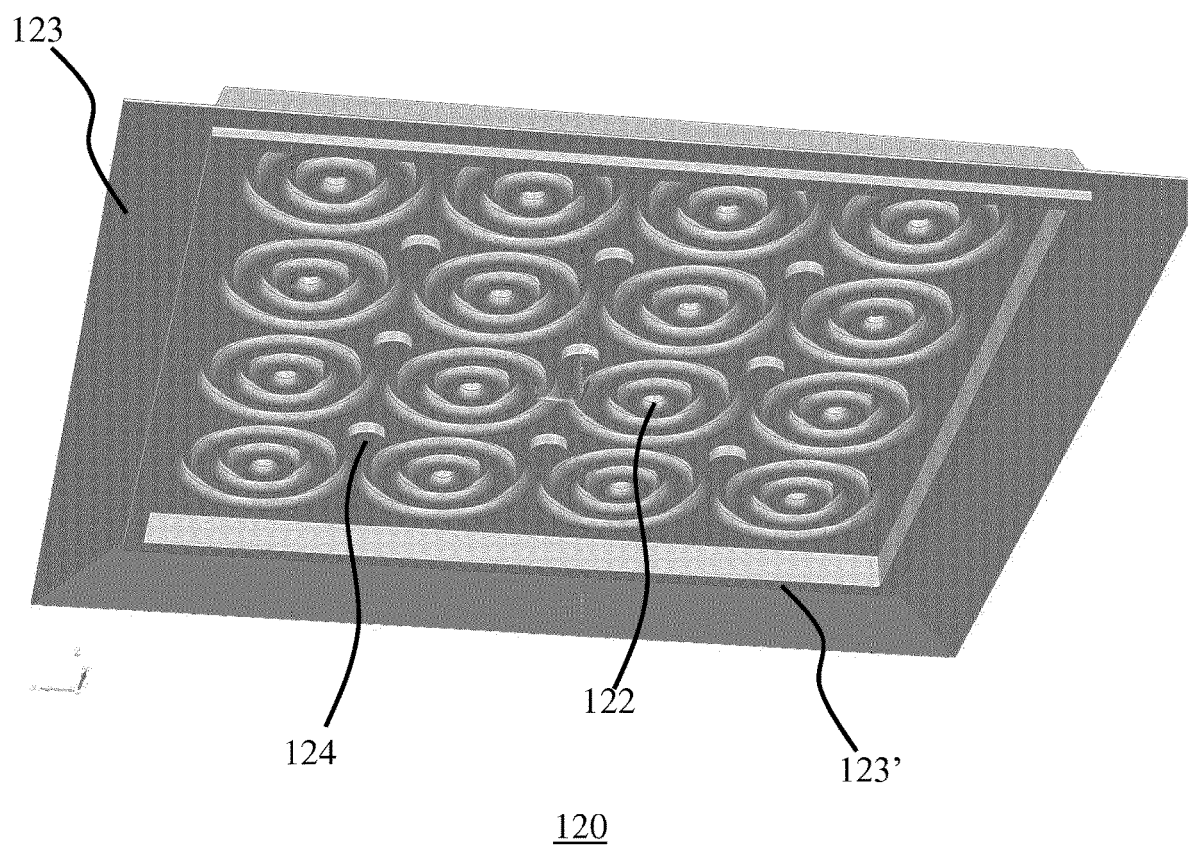
FIG. 3 schematically depicts a perspective view of a further aspect of such an ultrasound imaging system.

The ultrasound transducer array 100 may be adapted to transmit ultrasonic waves, e.g. ultrasound pulses, and receive (pulse) echo information as part of an ultrasound (diagnostic) imaging system 1. The ultrasound transducer array 100 according to the example embodiment comprises a body 120 having a mounting region 121 onto which the ultrasound transducer element tiles 101 are mounted. A detail of such a body 120 is schematically depicted in FIG. 3. Although not shown, the transducer surfaces of the ultrasound transducer element tiles 101 may be covered by an acoustic layer, sometimes referred to as an acoustic window, in order to protect the ultrasound transducer array from being directly contactable, thereby protecting the transducer array from damage, as well as to protect the body 50 of the subject, e.g. a patient, to be exposed to the ultrasound waves to be generated by the transducer array from being directly contacted by the transducer array, e.g. to protect the body 50 from accidental electrical shock. As is well-known per se, such an acoustic window may further provide impedance matching between the transducer array and the body. The acoustic layer may be made of any material or combinations of materials known to the skilled person for such purposes.

The mounting region 121 of the body may be flexible, which has the advantage that the mounting region 121 carrying the ultrasound transducer element tiles 101 may be deformed, e.g. to conform to a non-planar surface such as a contoured body of a patient to improve the quality of contact between the ultrasound transducer element tiles 101 and the patient's body 50. This is particularly relevant in case of large area ultrasound transducer arrays 100, where the array may need to conform to a large area of the patient's body, e.g. an area of several tens or hundreds of cm². For example, the mounting region 121 may comprise an elastomer, i.e. a rubbery material, to provide the mounting region 121 with the desired flexibility. Examples of such an elastomer include a polyolefin, a diene polymer or a polysiloxane such as PDMS, a co-polymer or block-copolymer comprising a polyolefin, a diene polymer or a polysiloxane or a blend thereof although embodiments are not limited thereto. Polybutadiene, polydimethylsiloxane (PDMS) and relatively soft polyether block amides (PEBA) commonly used in catheters, are specifically mentioned. A medical grade PDMS is particularly preferred. For example, the ultrasound transducer array 100 may be implemented as a flexible mat for conforming to the surface (i.e. skin of the body 50) of the subject.

Figure 4:
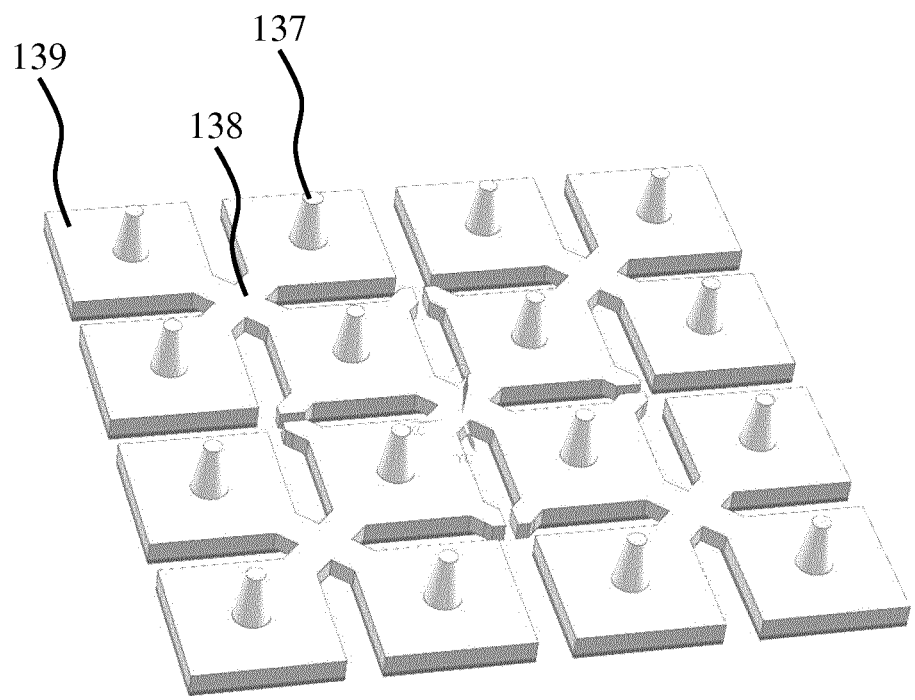
FIG. 4 schematically depicts a perspective view of a yet a further aspect of such an ultrasound imaging system.

The ultrasound transducer element tiles 101 may be directly mounted onto the mounting region 121 in some embodiments (not shown). In alternative embodiments, such as the embodiment schematically depicted in FIG. 2, the mounting region 121 may comprise a plurality of receiving portions 122 for receiving a support member onto which an ultrasound transducer element tile 101 may be mounted. A detail of such a support member is schematically depicted in FIG. 4. The support members may each comprise a pillar 137 that fits into one of the receiving portions 122 of the mounting region 121. Each pillar 137 carries a mounting portion 139 onto which the ultrasound transducer element tile 101 may be mounted. The support members may be made of a flexible material, e.g. a rubber-like material, and may be interconnected through mounting portions 139, e.g. to form a flexible mat 135 through interconnecting regions 138 in between adjacent mounting portions 139.

As shown in FIG. 4, each interconnecting region 138 connects four quadrants of mounting portions 139 that each have a corner interconnected to the interconnecting region 138. In this manner, each tile 101 will exhibit at least two degrees of rotational freedom, such that a good conformal contact with the body 50 of the subject can be achieved when the pressure in the space 110 is reduced by evacuation of a portion of air as explained in more detail below, with the resulting downward force on the mounting portions 139 as transferred through the pillars 137 being translated into the desired conformal contact of the tiles 101 through these rotational degrees of freedom. In an alternative embodiment, the support member arrangement, e.g. mat 135 may be a rigid arrangement in which the mounting regions 139 are mounted on a flexible joint, e.g. a universal joint, a ball and socket joint, or the like.

The mounting region 121 may be delimited by a flexible lip 123 that is arranged to contact the subject upon placement of the ultrasound transducer array 100 on the subject. The lip 123 is flexible such that upon placement of the ultrasound transducer array 100 on the subject, the lip 123 seals a space 110 in between the mounting region 121 of the body 120 and the part of the subject's body 50 opposite the mounting region 121. The lip 123 may form an integral part of the body 120, or may be adhered or otherwise attached to the mounting region 121. The lip 123 may have any suitable shape that facilitates the formation of a sealed space 110 in between the ultrasound transducer element tiles 101 and the body 50 of the subject upon placement of the ultrasound transducer array 100 on this body. The flexible lip 123 may be made of any suitable material, e.g. an elastomer as described above. In an embodiment, the mounting region 121 and the flexible lip 123 are made of the same material, with the flexible lip 123 preferably being integral to the mounting region 121, i.e. being formed from a single piece of flexible material. In an embodiment as depicted in FIG. 3, the lip 123 may include an edge 123' or may be separated from the space 110 by the edge 123', which edge 123' engages with the subject to reinforce the mounting region 121 in case of the pressure in the space 110 being reduced. The edge 123' may further assist in forming a seal between the ultrasound probe 100 and the subject 1 such that an underpressure can be established in the space 110 as explained above.

The mounting region 121 of the body 120 may further comprise support portions 124 in between the receiving portions 122 that reinforce the mounting region 121 in case of the pressure in the space 110 being reduced. The mounting region 121 may be corrugated as schematically depicted in FIG. 2 such that the mounting region can act as a spring. Consequently, when a volume of air is evacuated from the space 110 through outlet 127, e.g. using a vacuum pump or the like, to create an underpressure in the space 110, the atmospheric pressure over the ultrasound transducer array 100 forces the sprung mounting region 121 against the body 50. As little as a 10% reduction in pressure in the space 110 may suffice to achieve a downward pressure of $1N/cm^2$ on the mounting region 121. It should be understood that the above described embodiment of the ultrasound transducer array 100 is by way of non-limiting examples only and that any ultrasound transducer array 100 comprising a plurality of ultrasound transducer tiles 101 that are independently adjustable such as to conform to a portion of the body 50 of a patient may be used in the context of the present invention.

Figure 5:
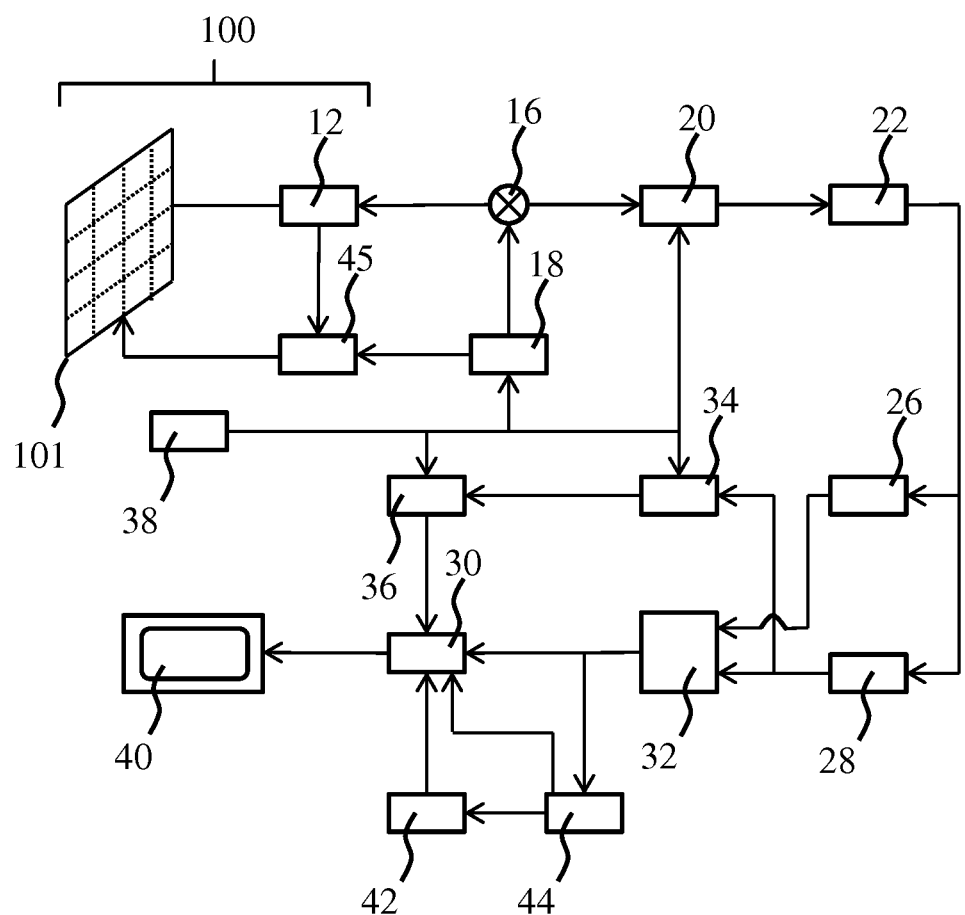
FIG. 5 schematically depicts a block diagram of an ultrasound imaging system according to an embodiment.

Now, upon returning to FIG. 1, the ultrasound imaging system 1 further comprises a user interface 10 such as a user console or the like for controlling the ultrasound transducer array 100. To this end, the user interface 10 typically comprises a processing arrangement that may include circuitry such as one or more dedicated or general purpose processors in order to control the ultrasound transducer array 100 in producing ultrasound pulses and receiving ultrasound pulse echo information from the ultrasound transducer array 100, which information may be processed by the processing arrangement in order to generate an ultrasound image, e.g. a 2-D or 3-D image, for display on the display device 40. A non-limiting example of such a user interface 10 will now be described in more detail with the aid of FIG. 5, which schematically depicts a block diagram of an example embodiment of the electronics that may be deployed to interface with and control the ultrasound transducer array 100 for the generation of ultrasound waves, e.g. ultrasound pulses, and reception of ultrasound echoes, e.g. pulse echoes, e.g. for diagnostic imaging purposes. The ultrasound transducer array 100 may be coupled to a microbeam former 12, which may be located in the ultrasound transducer array 100 in some embodiments, which controls transmission and reception of signals by the ultrasound transducer cells 100. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal, e.g. a user console device or the like, comprising a transmit/receive (T/R) switch 16 which switches between transmission and reception modes and protects the main beam former 20 from high energy transmit signals when a microbeam former is not present or used and the transducer array is operated directly by the main system beam former 20. The transmission of ultrasonic beams from the ultrasound transducer array 100 under control of the microbeam former 12 may be directed by a transducer controller 18 coupled to the microbeam former by the T/R switch 16 and the main system beam former 20, which receives input from the user's operation of the user interface 10 through control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control the aforementioned voltage source 45 for the ultrasound transducer array 110. For instance, the voltage source 45 sets the DC and AC bias voltage(s) that are applied to CMUT elements of a CMUT array, e.g. to operate the CMUT elements in collapse mode, as is well-known per se. The transducer controller 18 may be further adapted to control the voltage supply 45 such as to switch the ultrasound transducer element tiles 101 to a low-power mode, e.g. in response to a temperature sensor signal indicative of the ultrasound transducer element tiles 101 reaching a critical temperature.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer tiles 101 and/or from the individual ultrasound transducer elements of such ultrasound transducer tiles 101. In this way the signals received by thousands of transducer elements of an ultrasound transducer array 100 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information. As will be explained in more detail below, the signal processor 22 may further be adapted to register the individual images produced with the separate ultrasound transducer tiles 101 of the ultrasound transducer array 100.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the control panel 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 10 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 100 may not have 3D imaging capabilities and so on. Other variations will be apparent to the skilled person.

Figure 6:
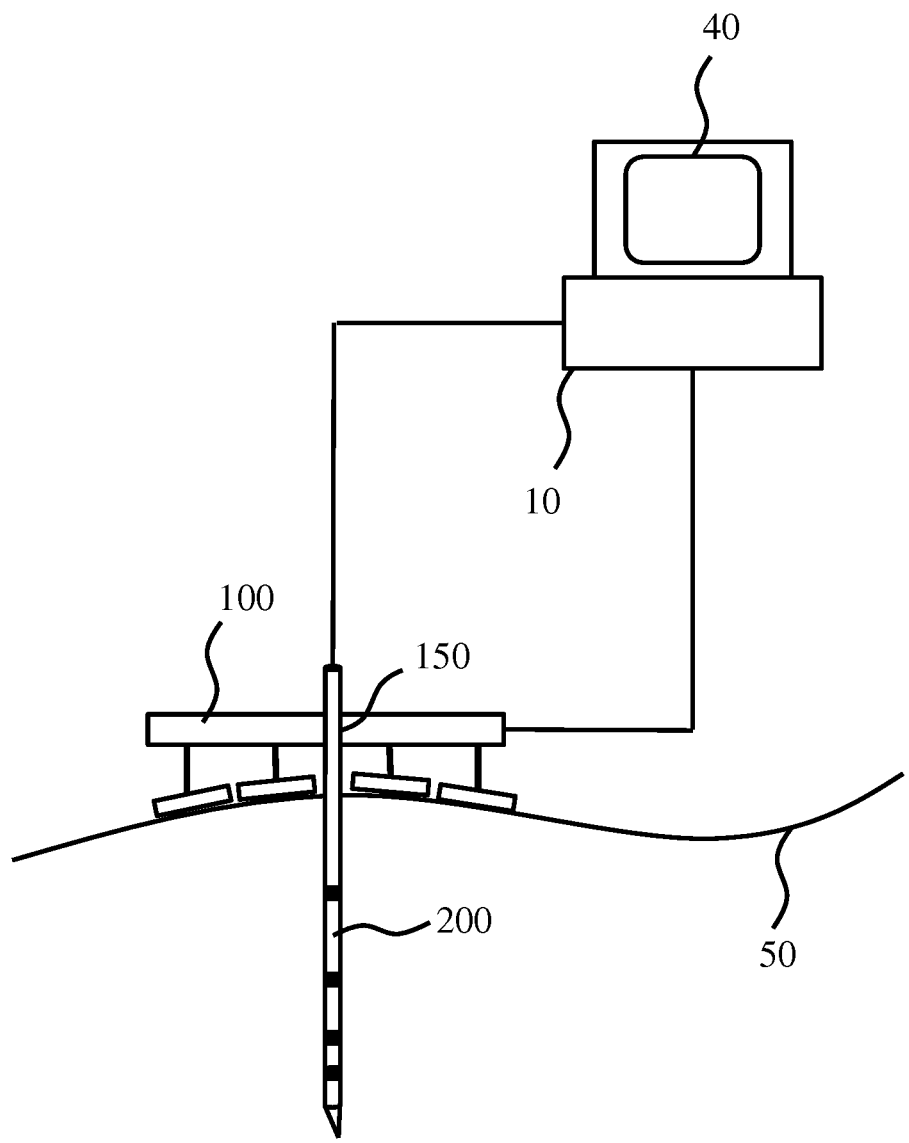
FIG. 6 schematically depicts an ultrasound imaging system according to another embodiment.

In an embodiment, the ultrasound transducer array 100 may be used to image a portion of the body 50 of the patient including a foreign object. This may be a static foreign object, such as for example a pacemaker, defibrillator, stent, or the like, or alternatively may be an interventional tool 200, which may form part of the ultrasound imaging system 1. Such an interventional tool 200 for example may be a catheter, a biopsy needle, or the like, which may be guided by a medical professional through the body 50 of the patient, in which case the ultrasound images generated with the ultrasound transducer array 100, e.g. an ultrasound transducer probe, may assist the medical professional in guiding the interventional tool 200 to the appropriate region within the body 50 of the patient, as such a region for instance may be clearly distinguishable within the ultrasound images generated with the ultrasound transducer array 100. The use (guidance) of such an interventional tool 200 may be independent of the ultrasound transducer array 100, as schematically depicted in FIG. 1, or alternatively, the use (guidance) of such an interventional tool 200 may be through the ultrasound transducer array 100 as schematically depicted in FIG. 6, in which case the ultrasound transducer array 100 may contain a guide channel 150 through which the interventional tool 200 may be guided into the body 50 of the patient. The latter embodiment has the benefit that it is more straightforward to capture the interventional tool 200 in the ultrasound images produced with the ultrasound transducer array 100 due to the spatial interrelationship between the ultrasound transducer array 100 and the interventional tool 200.

Figure 7:
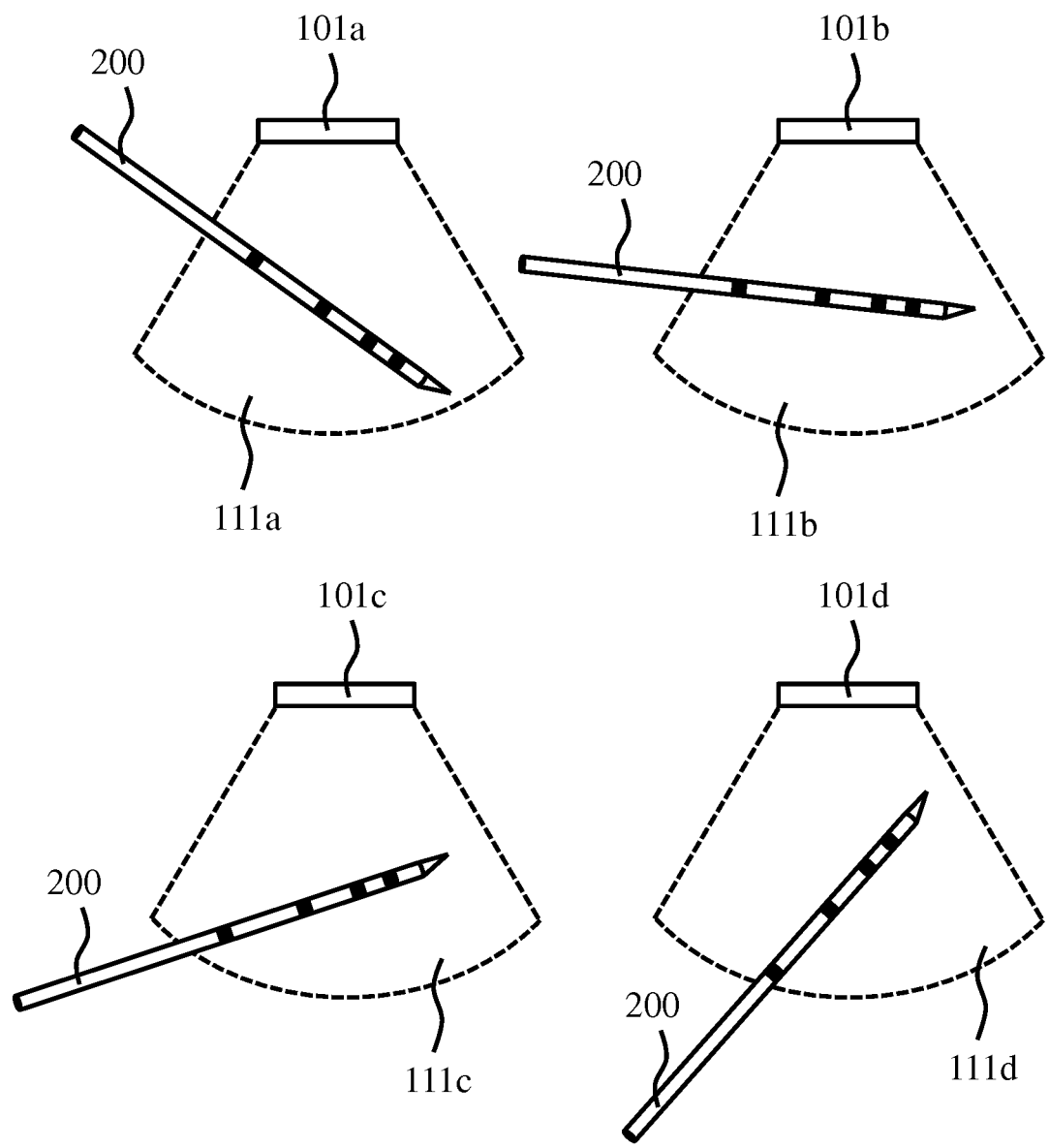
FIG. 7 schematically depicts unregistered ultrasound images captured with an ultrasound imaging system according to an embodiment.

Due to the independently adjustable nature of the ultrasound transducer tiles 101, the respective ultrasound images produced with the ultrasound transducer tiles 100 are not registered to the same reference frame, as different ultrasound transducer tiles 100 may have different unknown relative orientations to each other, as schematically depicted in FIGS. 1 and 6. Consequently, the respective ultrasound images captured with the respective ultrasound transducer tiles 101 in which a foreign body such as the interventional tool 200 is (at least partially) included, will depict the foreign body, e.g. the interventional tool 200, in different positions and orientations within the respective ultrasound images generated by the respective ultrasound transducer tiles 101. This is schematically depicted in FIG. 7, which schematically depicts four ultrasound images 111*a-d* generated with the ultrasound transducer tiles 101*a-d* respectively, in which the interventional tool 200 is at least partially captured in different positions and orientations within the respective ultrasound images 111*a-d*.

In embodiments of the present invention, the ultrasound imaging system 1, i.e. the processing arrangement of the user interface 10, e.g. the signal processor 26 and/or other processors of the user interface 10, are configured to register the respective ultrasound images 111 generated by the ultrasound transducer tiles 101 in order to generate a composite ultrasound image, i.e. an ultrasound image composed by at least those ultrasound images 111 in which at least a part of the foreign object, e.g. the interventional tool 200, is captured, and in which the position and orientation of the foreign object such as an interventional tool 200 in the individual ultrasound images 111 is aligned, e.g. superimposed. Embodiments are based on the insight that such foreign bodies may comprise a plurality of features 201-204 in a known spatial arrangement, e.g. a particular geometrical layout, which known spatial arrangement may be leveraged by the processing arrangement of the user interface 10 to register the individual ultrasound images 111.

In an embodiment, the processing arrangement may deploy object recognition algorithms to identify at least some of the respective features 201-204 in the respective ultrasound images 111 containing such features and to extract position and orientation information of the foreign object, e.g. the interventional tool 200, in each individual ultrasound image 111 utilizing the known spatial arrangement of the features 201-204 on the foreign body, e.g. features distributed along the shaft or the like of an interventional tool 200.

However, in a particularly advantageous embodiment, the interventional tool 200 comprises a plurality of ultrasound sensors 201-204 in a defined spatial arrangement on the interventional tool 200 (or other foreign body), which ultrasound sensors are communicatively coupled to the processing arrangement of the user interface 10 of the ultrasound imaging system 1. In this embodiment, the ultrasound sensors 201-204 may provide acoustic feedback information to the processing arrangement based on which the processing arrangement can determine the relative locations of the ultrasound sensors 201-204 in respect of a particular ultrasound transducer tile 101 responsible for generating an ultrasound transmission, e.g. an ultrasound pulse or the like, detected with at least some of the ultrasound sensors 201-204. Although four of such ultrasound sensors 201-204 are shown, it should be understood that any suitable number of ultrasound sensors may be provided on the interventional tool 200, as long as the interventional tool 200 comprises at least three of such ultrasound sensors. As will be readily understood by the skilled person, a minimum of three ultrasound sensors 201-204 is required to perform a triangulation calculation with the processing arrangement of the user interface 10 based on an ultrasound signal generated with one of the ultrasound transducer tiles 101, with additional ultrasound sensors in excess of the three ultrasound sensors improving the accuracy of such a triangulation method or alternatively providing redundancy that may be utilized in case of failure of one or more of the ultrasound sensors 201-204.

Such calculations for example may include determination of time of flight information of the ultrasound signal from its originating ultrasound transducer tile 101 to a particular ultrasound sensor detecting the ultrasound signal, ultrasound signal amplitude measurement information provided by one or more of the ultrasound sensors 201-204, and so on, which information may be utilized by the processing arrangement to determine a lateral and/or angular position of each ultrasound sensor, such that these respective positions of the ultrasound sensors may be translated into a position and orientation of the interventional tool 200 within a particular ultrasound image 111 based on the known spatial arrangement of the ultrasound sensors 201-204 on the interventional tool 200.

Figure 8:
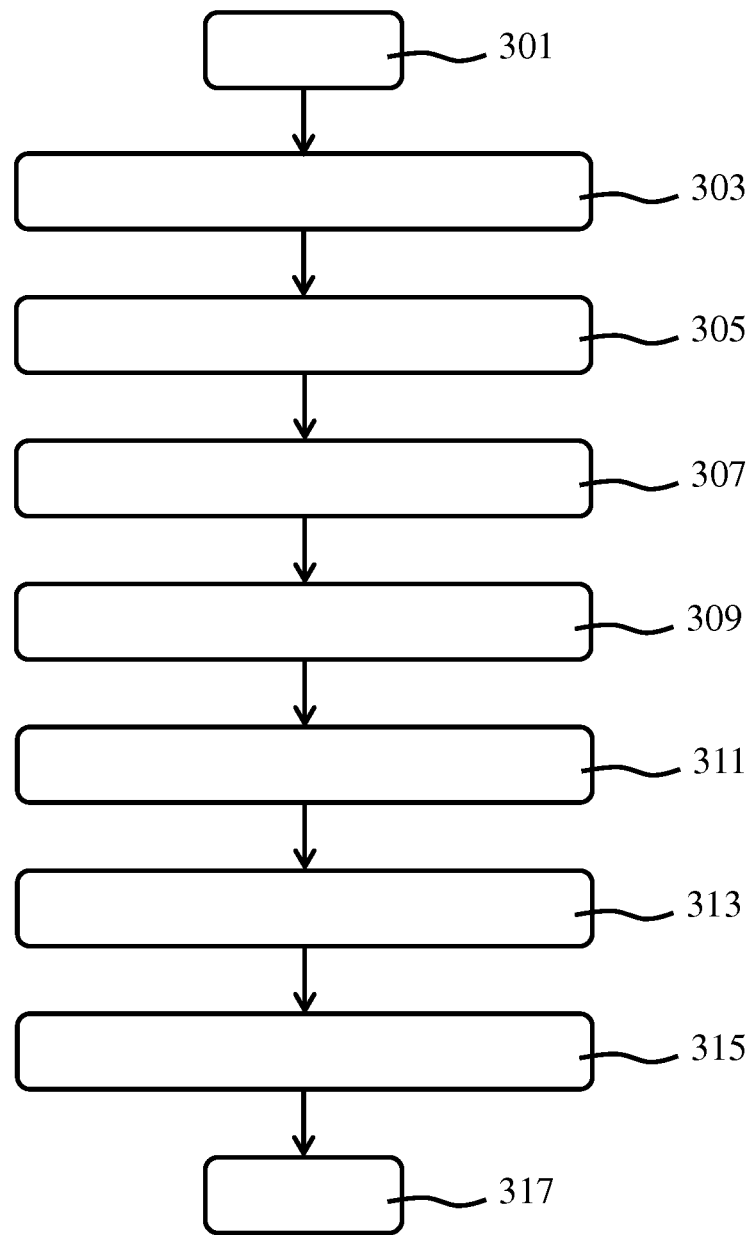
FIG. 8 depicts a flowchart of an ultrasound image registration method according to an embodiment.

An embodiment of an ultrasound image registration method 300 to be performed with the processing arrangement of the user interface 10 as part of a clinical workflow is depicted by the flowchart of FIG. 8. The method 300 starts in 301, for example by positioning a patient of a treatment table or the like and by switching on the ultrasound imaging system 1, after which the method 300 may proceed to 303 in which the interventional tool 200 is guided into an initial position within the body 50 of the patient in any suitable manner, for example under guidance of a conventional ultrasound transducer probe having one or more ultrasound transducer elements in a known orientation such that the respective ultrasound images generated with this conventional probe relate to a common reference frame, i.e. are registered.

Next, the ultrasound transducer array 100 may be positioned on the body 50 of the patient in 305, optionally using a special gel to improve the conformal contact between the respective ultrasound transducer tiles 101 of the ultrasound transducer array 100 and the portion of the body 50 onto which the ultrasound transducer array 100 is positioned, during which positioning each ultrasound transducer tile 101 adopts an orientation such that the tile conforms to the portion of the body 50 it contacts. As previously explained, due to the typically contoured nature of the body 50, this results in the respective ultrasound transducer tiles 101 adopting different orientations relative to each other such that the respective ultrasound images 111 generated with these ultrasound transducer tiles 101 require registering.

In 307, the respective ultrasound images 111 are acquired with the ultrasound transducer array 100. This may result in the acquisition of a number of images 111 in which the interventional tool 200 may be visible. This number of images 111 may equal the number of ultrasound transducer tiles 101, i.e. each ultrasound transducer tile 101 may have generated an ultrasound image 111 in which the part of the interventional tool 200 including at least some of the features, e.g. ultrasound sensors, 201-204 in the known spatial arrangement is visible or alternatively, the number of images 111 may be smaller than the number of ultrasound transducer tiles 101, i.e. only a subset of the ultrasound transducer tiles 101 produced ultrasound images 111 in which the part of the interventional tool 200 including at least some of the features, e.g. ultrasound sensors, 201-204 in the known spatial arrangement is visible. In the latter scenario, acquisition of the ultrasound images in 307 may further comprise selecting those ultrasound images 111, e.g. 111*a*-111*d*, in which the aforementioned part of the interventional tool 200 is visible for the image registration process, and discarding those ultrasound images 111 in which this part of the interventional tool 200 is not visible.

Next, the relative position and orientation of the interventional tool 200 is determined in 309 for each (selected) ultrasound image 111 using object recognition algorithms and/or acoustic feedback information provided by ultrasound sensors 201-204 as previously explained. As a simplified example based on the four ultrasound transducer tiles 101*a*-*d* generating four ultrasound images 111*a*-*d* each identifying the positions of the four features, e.g. ultrasound sensors, 201-204 in the respective ultrasound images 111*a*-*d*, the processing arrangement of the user interface 10 may estimate the location of each feature 201-204 in each ultrasound image 101*a*-*d* and express these estimated locations in a Cartesian coordinate (x, y, z) frame as follows:

$$P_{111a}(x,y,z) = \{(x_{1a}, y_{1a}, z_{1a}), (x_{2a}, y_{2a}, z_{2a}), (x_{3a}, y_{3a}, z_{3a}), (x_{4a}, y_{4a}, z_{4a})\}$$

$$P_{111b}(x,y,z) = \{(x_{1b}, y_{1b}, z_{1b}), (x_{2b}, y_{2b}, z_{2b}), (x_{3b}, y_{3b}, z_{3b}), (x_{4b}, y_{4b}, z_{4b})\}$$

$$P_{111c}(x,y,z) = \{(x_{1c}, y_{1c}, z_{1c}), (x_{2c}, y_{2c}, z_{2c}), (x_{3c}, y_{3c}, z_{3c}), (x_{4c}, y_{4c}, z_{4c})\}$$

$$P_{111d}(x,y,z) = \{(x_{1d}, y_{1d}, z_{1d}), (x_{2d}, y_{2d}, z_{2d}), (x_{3d}, y_{3d}, z_{3d}), (x_{4d}, y_{4d}, z_{4d})\}$$

Next, the processing arrangement may select one of the ultrasound images 111*a*-*d* (i.e. the orientation of one of the ultrasound transducer tiles 101*a*-*d*) as a reference in 311. In this example, image 111*a* is selected as the reference image, and the remaining ultrasound images 111*b*-*d* are subsequently registered in 313 relative to this reference image 111*a*. To this end, for each remaining ultrasound image, a transformation matrix T may be constructed that transforms the ultrasound image to the reference frame, i.e. the reference orientation of the ultrasound transducer tile 101 responsible for the generation of the reference ultrasound image 111, here ultrasound transducer tile 101*a* responsible for the generation of reference ultrasound image 111*a*:

$$P_R(x,y,z) = T_{111b \rightarrow R} \times P_{111b}(x,y,z)$$

$$P_R(x,y,z) = T_{111c \rightarrow R} \times P_{111c}(x,y,z)$$

$$P_R(x,y,z) = T_{111d \rightarrow R} \times P_{111d}(x,y,z)$$

where $T_{111b \rightarrow R}$, $T_{111c \rightarrow R}$ and $T_{111c \rightarrow R}$ are the transformations from ultrasound transducer tiles 101*b*, 101*c* and 101*d*, respectively, to the reference tile 101*a*. The respective transformations $T_{111b \rightarrow R}$, $T_{111c \rightarrow R}$ and $T_{111c \rightarrow R}$ are subsequently applied to the corresponding ultrasound images 111*a*-*d* to form a composite ultrasound image in 315 in which the respective positions of orientations of the interventional tool 200 in the ultrasound images 111 are transformed such that these respective positions and orientations are superimposed, as schematically depicted in FIG. 9, after which the method 300 may terminate in 317.

This registration method 300 ensures that the composite ultrasound image typically comprises a region 113 of high resolution around the interventional tool 200, thereby assisting a medical practitioner in accurately guiding the interventional tool 200 towards a region of interest within the body 50 of the patient. In order to maximize resolution of the region 113, the number of ultrasound images 111 on which the composite ultrasound image is based preferably is maximized, i.e. all ultrasound images 111 in which the relevant part of the interventional tool 200 is visible are included in the composite image although it should be understood that embodiments in which only a subset (i.e. not all) of the ultrasound images 111 in which the relevant part of the interventional tool 200 is visible are included in the composite image may also be contemplated. As will be readily understood by the skilled person, the registration method 300 may be carried out continuously in real-time, thereby providing updated image registration throughout the interventional tool 200 insertion process, e.g. in case the ultrasound transducer array 100 is displaced or otherwise adjusted during this insertion process.

At this point it is noted that the ultrasound transducer elements on the tiles 101 preferably are arranged in a 2-D matrix to obtain an (X,Y,Z) coordinate for each sensor 201-204. If there is only a 1-D array of ultrasound elements in each tile 101, it may be necessary to externally track the tile 101 and mechanically steer/pivot the tile 101 to obtain the position/angle at which the image plane of the image formed with the tile 101 contains one or more of the sensors 201-204.

Figure 9:
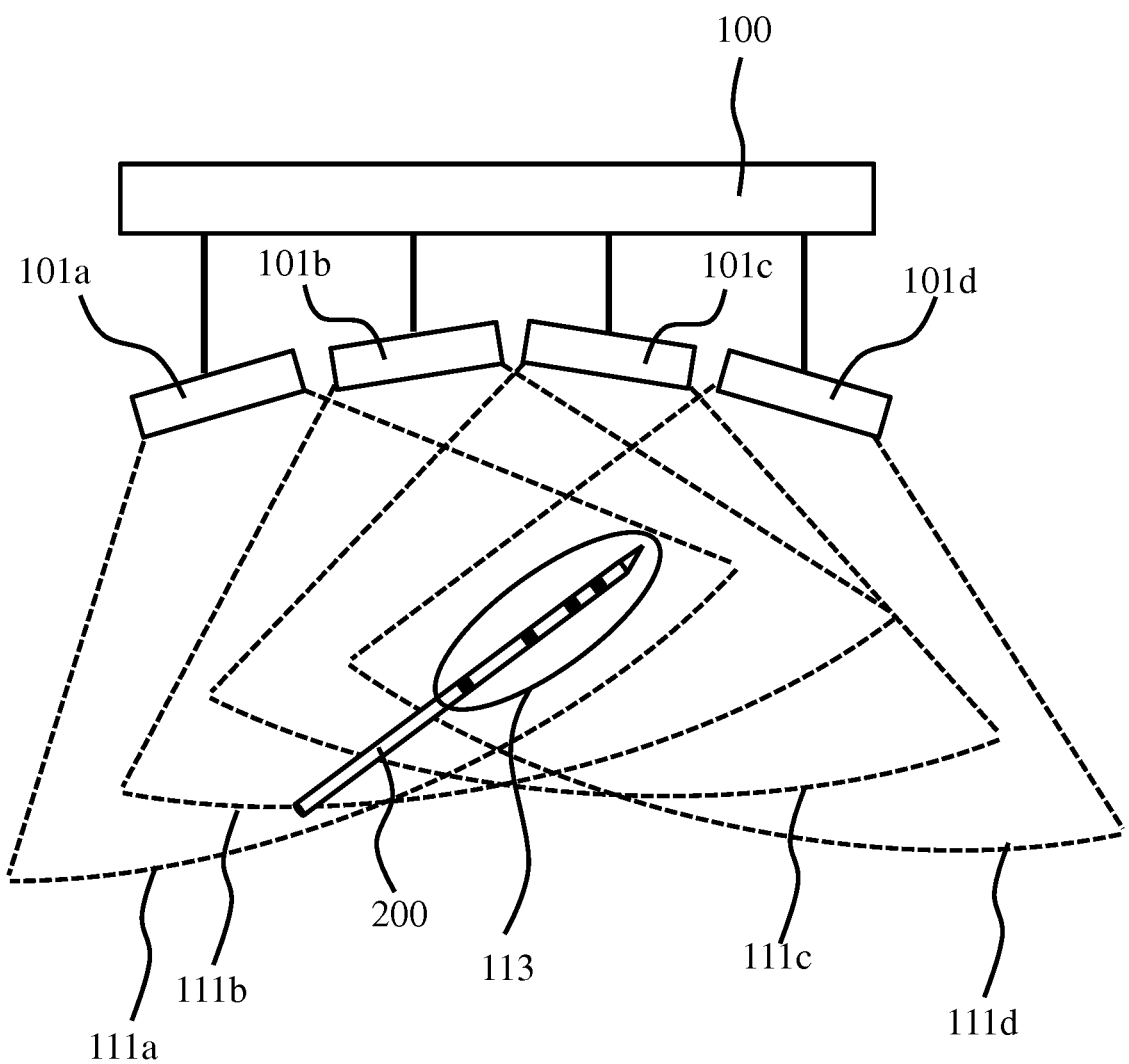
FIG. 9 schematically depicts a composite ultrasound image obtained with an ultrasound image registration method according to an embodiment.

In an embodiment, the user interface 10 of the ultrasound imaging system 1 may facilitate an imaging mode in which only the ultrasound transducer tiles 101 that are responsible for the generation of the ultrasound images 111 on which the composite image as schematically depicted in FIG. 9 is based are engaged in the subsequent imaging of the region of interest within the body 50 of the patient that includes the interventional tool 200. To this end, the user of the ultrasound imaging system 1 may provide the user interface 10, e.g. the control module 38, with a tactile or spoken instruction, e.g. by pressing a button or the like, by issuing a voice command, and so on, to which the ultrasound imaging system 1 response by only enabling the ultrasound transducer tiles 101 responsible for contributing to the composite image including the region 113. Consequently, a higher frame rate of the composite image can be achieved due to the fact that fewer ultrasound images 111 need to be acquired prior to composing the composite image, which further improves the resolution of the composite image (or stream of composite images) generated with the ultrasound imaging system 1. The frame rate may be further increased by enabling only the ultrasound transducer elements of these ultrasound transducer tiles that are responsible for producing an ultrasound signal, e.g. an ultrasound pulse or the like, responsible for the imaging of the interventional tool 200 (or another foreign body as previously explained).

Figure 10:
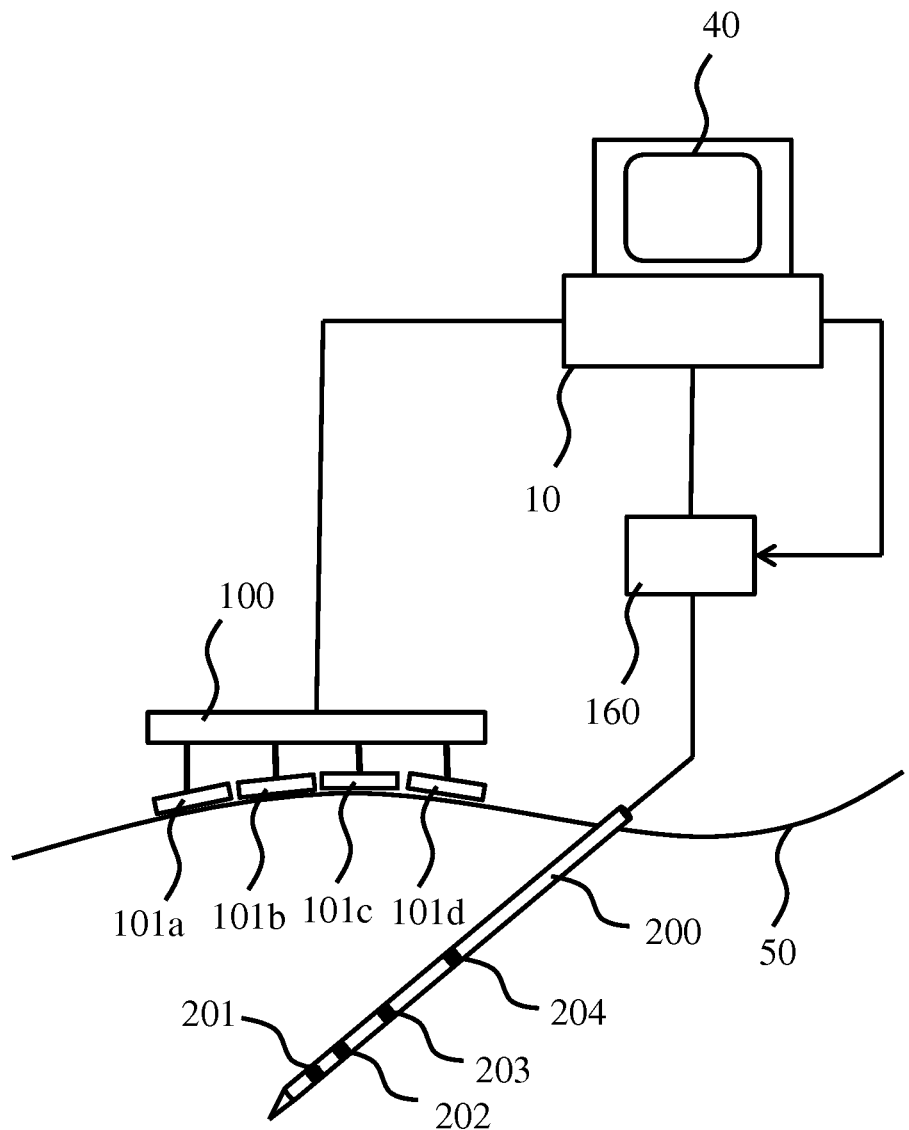
FIG. 10 schematically depicts an ultrasound imaging system according to yet another embodiment.

In an embodiment, as schematically depicted in FIG. 10, the interventional tool 200, i.e. the ultrasound sensors 201-204, may be communicatively coupled to the processing arrangement of the user interface 10 through a multiplexer (MUX) 160 controlled by the processing arrangement. Such a MUX 160 for example may be deployed in case the interventional tool 200 comprises additional ultrasound sensors in excess of the minimum number of required ultrasound sensors, i.e. (many) more than three ultrasound sensors 201-204. In such a scenario, several ultrasound transducer tiles 101 may each view a sufficient number of ultrasound sensors 201, 202, 203, 204 but different ultrasound transducer tiles may be able to see different ultrasound sensors. For example, ultrasound transducer tile 101a may be able to see ultrasound sensors 201, 202, 203, ultrasound transducer tile 101b may be able to see ultrasound sensors 201, 202, 203 and 204, whilst ultrasound transducer tile 101c may be able to see ultrasound sensors 202, 203, 204. In such a scenario, the ultrasound transducer tiles 101 may be registered in clusters, e.g. pairs, e.g. ultrasound transducer tiles 101a and 101b as a first pair, ultrasound transducer tiles 101b and 101c as a second pair, and so one, to include a fixed number of ultrasound sensors common to all ultrasound transducer tiles 101 in the cluster, e.g. three ultrasound sensors, for each registration. The optional MUX 160 may be used to select the appropriate subset of the ultrasound sensors 201-204 that are active during this registration process, for example in a scenario where the number of channels between the interventional tool 200 and the processing arrangement of the user interface 10 is smaller than the total number of ultrasound sensors 201-204 and the interventional tool 200, such that the appropriate subset of ultrasound sensors may be enabled by the MUX 160 by connecting this subset to the available channels.

The ultrasound imaging system 1 according to embodiments of the present invention may include the interventional tool 200 as previously explained. The ultrasound imaging system 1 according to embodiments of the present invention may be deployed in minimally invasive surgical procedure is by way of non-limiting example, such as needle-based procedures including but not limited to chorionic villus sampling (CVS), needle-based biopsies and nerve blocks for local anesthesia, where the ultrasound imaging system 1 according to embodiments of the present invention can support the correct positioning of the interventional tool 200 by providing a high-resolution imaging using the ultrasound transducer array 100, e.g. a large area ultrasound transducer array 100.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An ultrasound imaging system comprising:
an ultrasound transducer array comprising a plurality of ultrasound transducer tiles, each of said tiles having an independently adjustable orientation such as to conform an ultrasound transmitting surface of the tile to a region of a body; and
a user interface including a processing arrangement coupled to the ultrasound transducer array and configured to generate a composite ultrasound image by:
simultaneously registering a cluster of ultrasound transducer tiles comprising at least three ultrasound sensors in a defined spatial arrangement;
receiving respective ultrasound images from the cluster of ultrasound transducer tiles when the ultrasound transducer array is positioned on said region;
identifying, using a known spatial arrangement of a plurality of features of a foreign object located within the body, the position and location of said foreign object in a set of the received ultrasound images each comprising at least some of said features;
generating a composite ultrasound image from said set of received ultrasound images by superimposing the identified respective positions and orientations of the foreign object in the set of received ultrasound images, wherein said generating a composite ultrasound image comprises:
selecting one of said received ultrasound images as a reference ultrasound image;
defining the position and orientation of the foreign object in the reference ultrasound image as a reference;
generating, for each of the said received ultrasound images other than the reference ultrasound image, a transformation matrix for transforming the position and orientation of the foreign object in said received ultrasound image to the reference ultrasound image; and
transforming each of the said received ultrasound images other than the reference ultrasound image in accordance with the transformation matrix generated for said received ultrasound image.
2. The ultrasound imaging system of claim 1, wherein the foreign object is an interventional tool that forms part of the ultrasound system.
3. The ultrasound imaging system of claim 2, wherein the plurality of features comprises at least three ultrasound sensors in a defined spatial arrangement on the interventional tool, and wherein the processing arrangement is configured to:
- receive sensor signals from at least some of said at least three ultrasound sensors, said sensor signals corresponding to ultrasound signals generated with the ultrasound transducer array from which said received ultrasound images are generated; and wherein identification of the position and orientation of the interventional tool in the set of the received ultrasound images is based at least in part on said sensor signals.

4. The ultrasound imaging system of claim 3, wherein the processing arrangement configured to identify the position and orientation of the interventional tool in the set of the received ultrasound images based at least in part on said sensor signals is configured to:
- derive time of flight information and ultrasound signal amplitude information from said sensor signals; and
- at least identify the position and orientation of the interventional tool in at least a respective one of the received ultrasound images from said set at least partially based on the time of flight information and ultrasound signal amplitude information from said sensor signals corresponding to ultrasound signals from which said at least a respective one of the received ultrasound images is generated.

5. The ultrasound imaging system of claim 2, wherein the ultrasound transducer array comprises a guide channel for mounting the interventional tool in the ultrasound transducer array.

6. The ultrasound imaging system of claim 1, wherein the ultrasound sensors are coupled to the processing arrangement by a multiplexer controlled by said processing arrangement, wherein the processing arrangement is configured to enable the at least three common ultrasound sensors with the multiplexer during generation of the received ultrasound images with the ultrasound transducer tiles in said cluster.

7. The ultrasound imaging system of claim 1, wherein the processing arrangement is further configured to, in response to a user input received at the user interface, generate said second composite ultrasound image composed with the registered cluster of ultrasound transducer tiles.

8. The ultrasound imaging system of claim 7, wherein each ultrasound transducer tile comprises a plurality of ultrasound transducer elements, and wherein the processing arrangement is further configured to generate the second composite ultrasound image with a selection of the ultrasound transducer elements of at least some of the registered cluster of ultrasound transducer tiles, the selected ultrasound transducer elements contributing to the imaging of the foreign body.

9. A method of registering ultrasound transducer tiles of an ultrasound imaging system comprising an ultrasound transducer array comprising a plurality of said ultrasound transducer tiles, each of said tiles having an independently adjustable orientation such as to conform an ultrasound transmitting surface of the tile to a region of a body, the method comprising:
- simultaneously registering a cluster of ultrasound transducer tiles, the cluster of ultrasound transducer tiles comprising at least three ultrasound sensors in a defined spatial arrangement;
- receiving an ultrasound image from each of the ultrasound transducer tiles in the cluster of ultrasound transducer tiles when the ultrasound transducer array is positioned on said region;
- identifying, using a known spatial arrangement of a plurality of features of a foreign object located within the body, the position and location of said foreign object in a set of the received ultrasound images each comprising at least some of said features; and
- generating a composite ultrasound image from said set of received ultrasound images by superimposing the identified respective positions and orientations of the foreign object in the set of received ultrasound images, comprising the steps of: (i) selecting one of said received ultrasound images as a reference ultrasound image; (ii) defining the position and orientation of the foreign object in the reference ultrasound image as a reference; (iii) generating, for each of the said received ultrasound images other than the reference ultrasound image, a transformation matrix for transforming the position and orientation of the foreign object in said received ultrasound image to the reference ultrasound image; and (iv) transforming each of the said received ultrasound images other than the reference ultrasound image in accordance with the transformation matrix generated for said received ultrasound image.

10. The method of claim 9, wherein the foreign object is an interventional tool and the plurality of features comprises at least three ultrasound sensors in a known spatial arrangement on the interventional tool, the method further comprising receiving sensor signals from at least some of said at least three ultrasound sensors, said sensor signals corresponding to ultrasound signals generated with the ultrasound transducer array from which said received ultrasound images are generated; and wherein identifying the position and orientation of the interventional tool in the set of the received ultrasound images is based at least in part on said sensor signals.

11. The method of claim 10, further comprising:
- deriving time of flight information and ultrasound signal amplitude information from said sensor signals; and
- identifying the position and orientation of the interventional tool in at least a respective one of the received ultrasound images from said set at least partially based on the time of flight information and ultrasound signal amplitude information from said sensor signals corresponding to ultrasound signals from which said at least a respective one of the received ultrasound images is generated.

12. An ultrasound imaging system comprising:
- an ultrasound transducer array comprising a plurality of ultrasound transducer tiles, each of said of ultrasound transducer tiles having an independently adjustable orientation such as to conform an ultrasound transmitting surface of the tile to a region of a body, and each of said of ultrasound transducer tiles comprising a plurality of ultrasound transducer elements; and
- a user interface including a processing arrangement coupled to the ultrasound transducer array and configured to register the ultrasound transducer tiles by:
  - receiving respective ultrasound images from at least some of the ultrasound transducer tiles when the ultrasound transducer array is positioned on said region;
  - identifying, using a known spatial arrangement of a plurality of features of a foreign object located within the body, the position and location of said foreign object in a set of the received ultrasound images each comprising at least some of said features;

generating a composite ultrasound image from said set of received ultrasound images by superimposing the identified respective positions and orientations of the foreign object in the set of received ultrasound images, wherein said generating a composite ultrasound image comprises:
  selecting one of said received ultrasound images as a reference ultrasound image;
  defining the position and orientation of the foreign object in the reference ultrasound image as a reference;
  generating, for each of the said received ultrasound images other than the reference ultrasound image, a transformation matrix for transforming the position and orientation of the foreign object in said received ultrasound image to the reference ultrasound image; and
  transforming each of the said received ultrasound images other than the reference ultrasound image in accordance with the transformation matrix generated for said received ultrasound image;
simultaneously registering a cluster of ultrasound transducer tiles, wherein the received ultrasound images generated with the ultrasound transducer tiles in said cluster of ultrasound transducer tiles contains at least three ultrasound sensors in a defined spatial arrangement; and
generating a second composite ultrasound image composed with a plurality of ultrasound images obtained with the registered cluster of ultrasound transducer tiles, wherein the processing arrangement is configured to generate the second composite ultrasound image with a selection of the ultrasound transducer elements of at least some of the registered cluster of ultrasound transducer tiles, the selected ultrasound transducer elements contributing to the imaging of the foreign body.

* * * * *